(12) United States Patent
Cox

(10) Patent No.: US 6,786,876 B2
(45) Date of Patent: Sep. 7, 2004

(54) MEDICAL DEVICES HAVING FULL OR PARTIAL POLYMER COATINGS AND THEIR METHODS OF MANUFACTURE

(75) Inventor: Brian J. Cox, Laguna Niguel, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 155 days.

(21) Appl. No.: 10/177,651

(22) Filed: Jun. 20, 2002

(65) Prior Publication Data

US 2003/0023190 A1 Jan. 30, 2003

Related U.S. Application Data

(60) Provisional application No. 60/299,645, filed on Jun. 20, 2001.

(51) Int. Cl.[7] .......................... A61B 5/00; A61M 25/00
(52) U.S. Cl. ..................................... 600/585
(58) Field of Search .......................... 600/585; 427/2.1, 427/532, 2.22, 341, 353, 372.2, 385.5, 388.4, 460, 491, 508, 520, 533, 534, 535, 536; 604/264, 96.01; 428/423.1, 457; 623/23.29

(56) References Cited

U.S. PATENT DOCUMENTS

| | | |
|---|---|---|
| 3,969,552 A | 7/1976 | Malofsky et al. |
| 4,147,821 A | 4/1979 | Young |
| 4,263,372 A | 4/1981 | Emmons et al. |
| 4,435,476 A | 3/1984 | Phillips et al. |
| 4,504,528 A | 3/1985 | Zucker et al. |
| 4,541,980 A | 9/1985 | Kiersarsky et al. |
| 4,556,701 A | 12/1985 | Schindler et al. |
| 4,705,584 A | 11/1987 | Lauchenauer |
| 4,729,914 A | 3/1988 | Kliment et al. |
| 4,784,159 A | 11/1988 | Szilagyi |
| 4,795,472 A * | 1/1989 | Crowninshield et al. . 623/23.29 |
| 5,095,915 A | 3/1992 | Engelson |
| 5,129,890 A | 7/1992 | Bates et al. |
| 5,217,026 A | 6/1993 | Stoy et al. |
| 5,235,964 A | 8/1993 | Abenaim |
| 5,290,585 A | 3/1994 | Elton |
| 5,331,027 A | 7/1994 | Whitbourne |
| 5,333,620 A | 8/1994 | Moutafis et al. |
| 5,437,288 A | 8/1995 | Schwartz et al. |

(List continued on next page.)

FOREIGN PATENT DOCUMENTS

| | | |
|---|---|---|
| EP | 0 652 026 A1 | 5/1995 |
| EP | 0 680 351 B1 | 11/1995 |
| WO | WO 9211877 | 7/1992 |
| WO | WO 93/04722 | 3/1993 |
| WO | WO 00/06239 | 2/2000 |
| WO | WO 0065143 | 11/2000 |
| WO | WO 96/38193 | 12/2000 |

*Primary Examiner*—Mary Beth Jones
*Assistant Examiner*—Brian Szmal
(74) *Attorney, Agent, or Firm*—Robert D. Buyan; Stout, Uxa, Buyan & Mullins, LLP

(57) ABSTRACT

Medical devices for insertion into the body of human or veterinary patients, wherein the device comprises a) a working element (e.g. a wire, a guidewire, a tube, a catheter, a cannula, a scope (e.g., rigid or flexible endoscope, laparoscope, sigmoidoscope, cystoscope, etc.) a probe, an apparatus for collecting information from a location within the body (e.g., an electrode, sensor, camera, scope, sample withdrawal apparatus, biopsy or tissue sampling device, etc.) which has an outer surface and b) a continuous or non-continuous coating on the outer surface of the working element. The outer surface of the working element is prepared to create a surface topography which promotes mechanical or frictional engagement of the coating to the working element. In some embodiments the coating is a lubricious coating and/or a swellable coating.

57 Claims, 3 Drawing Sheets

U.S. PATENT DOCUMENTS

| | | |
|---|---|---|
| 5,441,488 A | 8/1995 | Shimura et al. |
| 5,443,455 A | 8/1995 | Hergenrother et al. |
| 5,443,907 A | 8/1995 | Slaikeu et al. |
| 5,573,520 A | 11/1996 | Schwartz et al. |
| 5,700,559 A | 12/1997 | Sheu et al. |
| 5,741,429 A | 4/1998 | Donadio, III et al. |
| 5,746,701 A | 5/1998 | Noone |
| 5,749,968 A | 5/1998 | Melanson et al. |
| 5,750,206 A | 5/1998 | Hergenrother et al. |
| 5,833,632 A | 11/1998 | Jacobsen et al. |
| 5,840,046 A | 11/1998 | Deem |
| 5,891,057 A | 4/1999 | Chaisson et al. |
| 5,984,878 A | 11/1999 | Engelson |
| 6,027,863 A | 2/2000 | Donadio, III |
| 6,033,394 A | 3/2000 | Vidlund et al. |
| 6,080,488 A | 6/2000 | Hostettler et al. |
| 6,086,548 A | 7/2000 | Chaisson et al. |
| 6,110,164 A | 8/2000 | Vidlund |
| 6,149,978 A | 11/2000 | Bladel et al. |
| 6,162,310 A | 12/2000 | Tseng |
| 6,176,849 B1 | 1/2001 | Yang et al. |

\* cited by examiner

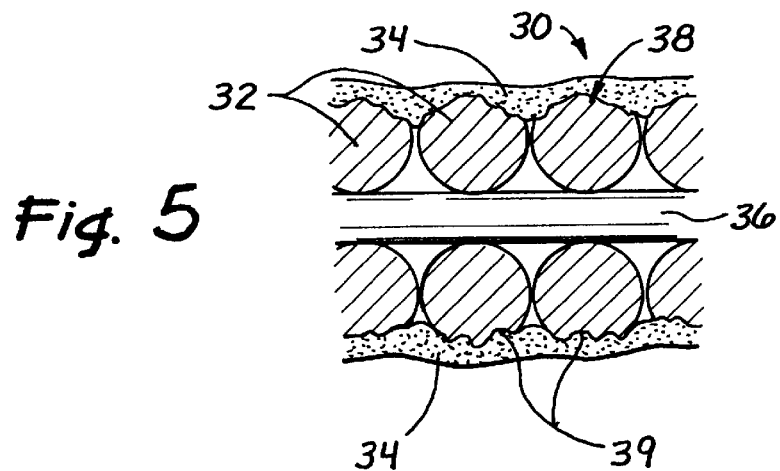
Fig. 5
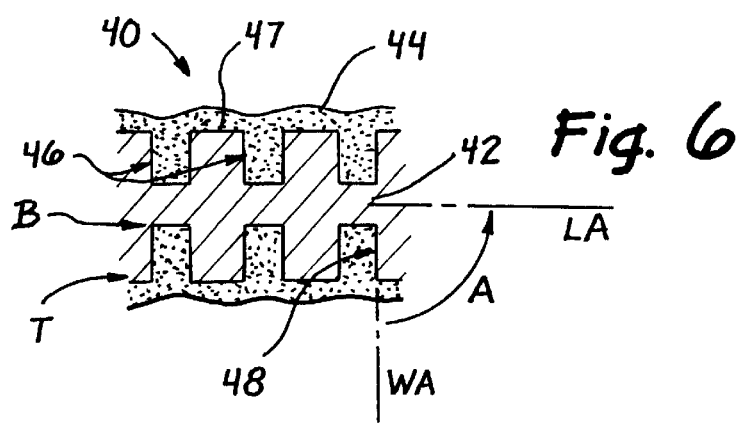
Fig. 6
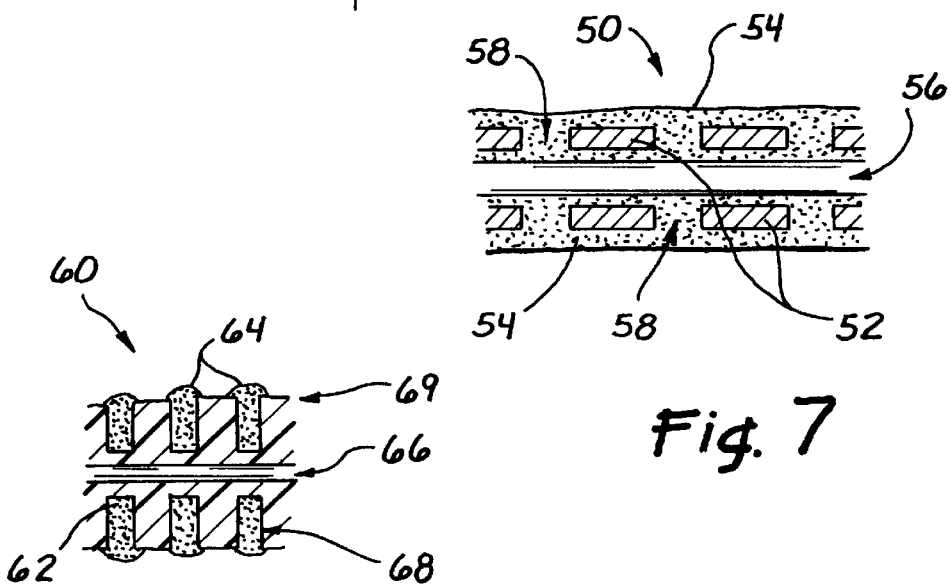
Fig. 7
Fig. 8

Fig. 9B (ALT)

MEDICAL DEVICES HAVING FULL OR PARTIAL POLYMER COATINGS AND THEIR METHODS OF MANUFACTURE

RELATED INVENTION

This patent application claims priority to U.S. Provisional Patent Application Serial No. 60/299,645 filed on Jun. 20, 2001, which is expressly incorporated herein by reference.

FIELD OF THE INVENTION

The present invention relates generally to biomedical devices and methods for manufacturing biomedical devices and more particularly to biomedical devices that have full or partial polymer coatings and their methods of manufacture.

BACKGROUND OF THE INVENTION

Medical instruments are frequently coated with various polymers to reduce sliding friction (e.g. by lubricity) and provide other performance enhancing characteristics. Obtaining adequate adherence of the polymer coating to the instrument substrate is a problem in many instances and particularly when a hydrogel is coated on a metal substrate.

Various hydrophylic and hydrophobic polymer coatings and their methods of application have been described in U.S. Pat. No. 4,263,372 Method of coating and/or impregnating porous substrates, and products obtained thereby (Emmons et al.); U.S. Pat. No. 4,435,476 Method of making an abrasion resistant coating on a solid substrate and articles produced thereby (Phillips et al.); U.S. Pat. No. 4,504,528 Process for coating aqueous fluoropolymer coating on porous substrate (Zucker et al.); U.S. Pat. No. 4,541,980 Methods of producing plastic-coated metallic members (Kiersarsky et al.); U.S. Pat. No. 4,705,584 Application of polymeric materials to substrates (Lauchenauer); U.S. Pat. No. 4,729,914 Hydrophilic coating and substrate coated therewith (Kliment et al.); U.S. Pat. No. 4,784,159 Process for making an implantable device having a plasma sprayed metallic porous surface (Szilagyi); U.S. Pat. No. 5,095,915 Guidewire with flexible distal tip (Engelson); U.S. Pat. No. 5,129,890 Hydrophilically coated flexible wire guide (Bates et al.); U.S. Pat. No. 5,235,964 Flexible probe apparatus (Abenaim); U.S. Pat. No. 5,290,585 Lubricious hydrogel coatings (Elton); U.S. Pat. No. 3,969,552 Process for impregnating porous articles (Malofsky et al.); U.S. Pat. No. 4,147,821 Impregnation of porous articles (Young); U.S. Pat. No. 4,556,701 Impregnate compositions for porous substrates (Schindler et al.); U.S. Pat. No. 5,333,620 High performance plastic coated medical guidewire (Moutafis et al.); U.S. Pat. No. 5,441,488 Medical tool having lubricious surface in a wetted state and method for production thereof (Shimura et al.); U.S. Pat. No. 5,443,455 Guidewire and method of pretreating metal surfaces for subsequent polymer coating (Hergenrother et al.); U.S. Pat. No. 5,443,907 Coating for medical insertion guides (Slaikeu et al.); U.S. Pat. No. 5,437,288 Flexible catheter guidewire (Schwartz et al.); U.S. Pat. No. 5,573,520 Flexible tubular device for use in medical applications (Schwartz et al.); U.S. Pat. No. 5,749,968 Device for priming for improved adherence of gels to substrates (Melanson et al.); U.S. Pat. No. 5,750,206 Method of pretreating metal surfaces for subsequent polymer coating (Hergenrother et al.); U.S. Pat. No. 5,833,632 Hollow guide wire apparatus catheters (Jacobsen et al.); U.S. Pat. No. 5,700,559 Durable Hydrophilic Surface Coatings (Sheu et al.); U.S. Pat. No. 6,080,488 Process for preparation of slippery, tenaciously adhering, hydrophilic polyurethane hydrogel coating . . . medical devices (Hostettler et al.); U.S. Pat. No. 6,149,978 Coating of porous, hydrophobic substrates with thermoplastic fluoropolymers (Bladel et al.); U.S. Pat. No. 6,162,310 Method for producing porous sponge like metal (Tseng); U.S. Pat. No. 6,176,849 Hydrophilic lubricity coating for medical devices comprising a hydrophobic top coat (Yang et al.); U.S. Pat. No. 5,840,046 Guidewire Having Hydrophilic Coating (Deem); U.S. Pat. No. 5,984,878 (Multi-Coating Stainless Steel Guidewire (Engelson) as well as PCT International Patent Publications WO 92/11877 Biocompatible abrasion resistant coated substrates (Fan et al.) and WO 00/65143 Process for coating a perforated substrate (Munro et al.), all f which are expressly incorporated herein by reference.

One reason for applying polymer coatings to insertable medical devices is to impart lubricity to, or to lower the coefficient of friction of, the outer surface of the device. Some of these polymer coatings, such as fluorocarbon coatings (e.g., polytetrafluoroethylene) provide a lubricious hydrophobic surface while others such as swellable hydrogels are hydrophilic and become lubricious after coming in contact with liquid (e.g., blood or other body fluid).

For example, U.S. Pat. No. 5,573,520 (Schwartz et al.) describes a flexible tubular member encased by a fluid tight polymer covering, including a hydrogel, for use as a guidewire, catheter or introducer. However, the polymer covering is only described as covering either the inside surface or the outside surface for the purposes of a fluid tight sealing of aperatures or for providing lubricity. As described earlier, these benefits of coatings are known in the art. However, Schwartz et al. does not describe the coating to be integral to the wall of the device or there being any sort of interlock or other improved attachment of the coating.

Also, U.S. Pat. No. 5,840,046 (Deem) describes guidewires having hydrophilic coatings, such as hydrophilic polysaccharides (e.g., hyaluronic acid or chondroitin sulfate). The guidewires are made of wire which is helically coiled about a core member. The spacing between adjacent coils of the wire is wide enough to allow the coating to flex along with the coil but narrow enough to prevent the coating from penetrating into an annular space that exists between the coiled wire and the inner core member.

SUMMARY OF THE INVENTION

The present invention provides novel polymer coated medical instruments including guidewires, catheters, cannula, endoscopes and other instruments for insertion into the body.

In accordance with the present invention, there are provided medical devices that are insertable into the bodies of human or veterinary patients, each such device comprising a) a working element having an outer surface and b) a polymer coating disposed on at least a portion of the outer surface of the working element, wherein the outer surface of the working element has a topography characterized by surface features which deter longitudinal slippage of the coating over the outer surface and or which result in some mechanical engagement or interlock between coating and the working element. In this regard, the outer surface of the working element may have one or more cavities formed therein, at least some of those cavities having side walls which are disposed at angles of about 75 or more degrees relative to the longitudinal axis of the working element (or relative to the outer surface of the working element immediately adjacent to those side walls) and wherein at least a portion of the polymer coating extends into at least some of the cavities so as to deter separation of the polymer coating from the working element. In this manner the present invention may provide an alternative to the use of adhesive coatings or chemical adhesive layers such as the "tie layers" described in U.S. Pat. No. 5,749,837 (Palermo), which is expressly incorporated herein by reference.

Further in accordance with the invention, the cavities formed in the outer surface of the working element may comprise holes, grooves, a continuous helical or curved groove, slots, pores, apertures or other external surface features to provide a substantial improvement in the adherence of a polymer coating. The coating fills into at least some of the cavities to form a mechanical bond or interlock with the working element. To accomplish such mechanical bond or interlock, the cavities are preferably at least about 0.001 inch deep and may extend completely through the working element forming a through-hole or slot. In at least some embodiments, it is preferable that the polymer coating to penetrate to a depth below the outer surface that is at least about 25%, and more preferably at least about 50%, of the total thickness of the polymer coating on that portion of the device. Thus, for example, in a region where the polymer coating is a total of 100 mills thick, it will be preferable for the coating to penetrate into cavities at least about 25 mills below the outer surface and more preferably at about 50 mills below the outer surface. The coating need not be for the purpose of providing lubricity, although such is one purpose for the invention. Indeed, the coating may serve any purpose, such as the creating of a biocompatible barrier to insulate the patients body from toxic, infectious or non-biocompatible materials on the underlying surface of or within the device.

Still further in accordance with the invention the working element may comprise any apparatus or device that is insterable into the body, including but not limited to a wire, a guidewire, a tube, a catheter, a cannula, a scope (e.g., rigid or flexible endoscope, laparoscope, sigmoidoscope, cystoscope, etc.) a probe, an apparatus for collecting information from a location within the body (e.g., an electrode, sensor, camera, scope, sample withdrawal apparatus, biopsy or tissue sampling device, etc.). The working element's outer surface may be made from a radiopaque, biocompatible metal such as platinum, gold, tungsten, nitinol, elgiloy, stainless steel, or tantalum but may be made of a polymer impregnated or otherwise modified to be visible under x-rays by various means known in the art. Alternatively, the working element's outer surface may be made of a plastic or polymer material which, in at least some embodiments, may be visualized under ultrasound, magnetic resonance imaging, radiographic imaging or other medical visualization methods known in the art.

Still further in accordance with the present invention, the polymer coating may comprise a material that is lubricious or has a low coefficient of friction, such as polytetrafluoroethylene (e.g. Teflon). Also, the polymer coating may comprise a hydrophilic polymer (i.e. hydrogel) that creates a lubricious surface after being exposed to a liquid (e.g., blood or other body fluid). It is preferable that the hydrogel be polymerized from ethylenically unsaturated monomers. In some cases, environmentally responsive hydrogels may be used such as that described in cozening U.S. patent application Ser. No. 09/804,935 entitled Hydrogels That undergo Volumetric Expansion In Response To Changes In Their Environment And Their Methods Of manufacture And Use. Specific examples of hydrogels that may be used include those described in U.S. Pat. No. 4,729,914 (Kliment), U.S. Pat. No. 5,290,585 (Eiton), U.S. Pat. No. 5,331,027 (Whitboume), U.S. Pat. No. 6,080,488 (Hostettlerel al.), U.S. Pat. No. 6,176,849 (Yang et al.) and pending U.S. patent application Ser. No. 09/804,935 entitled Hydrogels That undergo Volumetric Expansion In Response To Changes In Their Environment And Their Methods Of manufacture And Use, each of which is expressly incorporated herein by reference. In some embodiments of the invention, the polymer may be formed about the outer surface of the working element in a non-continuous manner (e.g., in discrete ridges, bumps or areas) or such polymer coating may be disposed in a manner that forms a generally smooth continuous polymer coating surface. In some embodiments, the polymer coating may be radioopaque.

Even further aspects of this invention will be come apparent to those of skill in the art upon reading of the detailed description of exemplary embodiments set forth herebelow.

BRIEF DESCRIPTION OF THE DRAWINGS

FIG. 5 is a partial longitudinal sectional view of another guidewire which has a polymer coating disposed thereon in accordance with the present invention.

FIG. 6 is a partial longitudinal sectional view of a solid, elongate probe which has a polymer coating disposed thereon in accordance with the present invention.

FIG. 7 is a partial longitudinal sectional view of an elongate tubular device such as a catheter, scope, cannula, introducer, sheath, or the like having a polymer coating disposed thereon in accordance with the present invention.

FIG. 8 is a partial longitudinal sectional view of an elongate device having another polymer coating disposed thereon in accordance with the present invention.

DETAILED DESCRIPTION OF THE INVENTION

Figure 1:
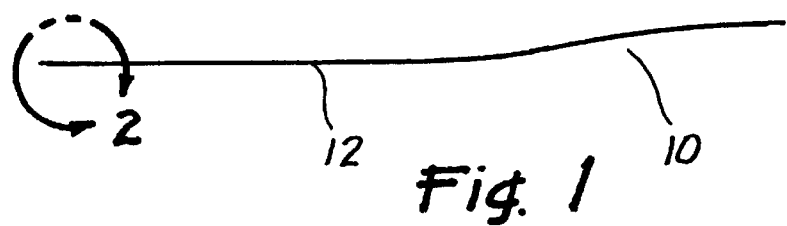
FIG. 1 is a perspective view of a guidewire which has a polymer coating disposed thereon in accordance with the present invention.

The invention is described herebelow with reference to certain examples or embodiments as shown in the accompanying drawings. These examples or embodiments are not limiting, but rather are merely exemplary of some of the ways in which the present invention may be reduced to practice.

FIGS. 1–4 show an example of a guidewire 10 that bears a polymer coating according to this invention. As shown, the guidewire 10 comprises an elongate, flexible body 12 having a blunt distal tip member 18 positioned at its distal end. The guidewire body 12 comprises a continuous, tightly wound, helical coil formed of wire 14. A solid or tubular core member 16 may optionally be disposed within the helically wound wire 14. Pores 22 are formed in at least the outer surface of the helically coiled wire 14. A polymer coating 20 is disposed on the outer surface of the guidewire body 12, as shown. A portion of such polymer coating extends into some of the pores 22 at the surface of the wire 14, as can be appreciated from the showing of FIG. 4. The wire 14 is made of a porous material or is treated to have a porous surface.

If a porous material is used, secondary cutting or surface treatment of the wire 14 may be avoided or reduced. Microporous metal can be fabricated by sintering process, plasma spraying (see U.S. Pat. No. 4,784,159) or other means known in the art. One biologically compatible, porous, sintered metal is commercially available from Implex Corp., Allendale, N.J. under the tradename Hedrocel. In the device shown in FIGS. 1–4, the coating 20 has impregnated the pores 22 of the wire 14 to form a mechanical bond. One example of an acceptable coating is a fluoropolymer coating and applied by the methods described by Bladel et al. in the U.S. Pat. No. 6,149,978. Another example is an acceptable coating is a swellable hydrogel. Optionally, the coating may be modified, impregnated or otherwise combined with a variety of pharmacologic or bioactive substances (e.g. chemicals, drugs, proteins, peptides, or growth factors) to impart anti-infective, anti-thrombogenic or other desirable interactions with the body.

Although the example shown in FIGS. 1–4 is a guidewire 10, it is to be appreciated that the working element on which the coating 20 is applied may comprise any insertable medical device, including but not limited to a catheter, cannula, probe, scope, electrode, other wire, sensor, etc.

Figure 2:
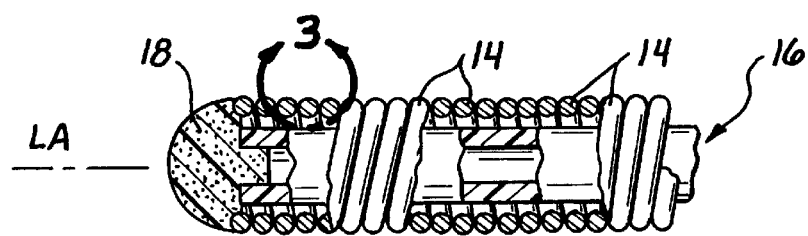
FIG. 2 is an enlarges, cut-away view of portion 2 of the guidewire of FIG. 1.
Figure 3:
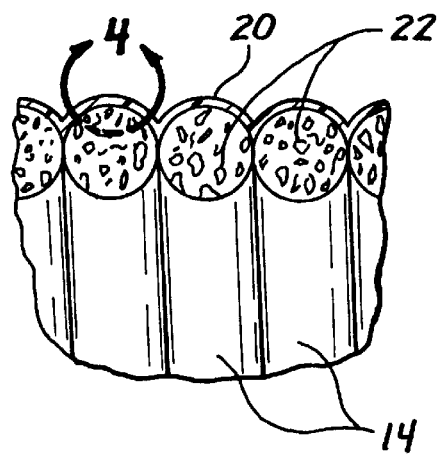
FIG. 3 is an enlarged view of portion 3 of FIG. 2.
Figure 4:
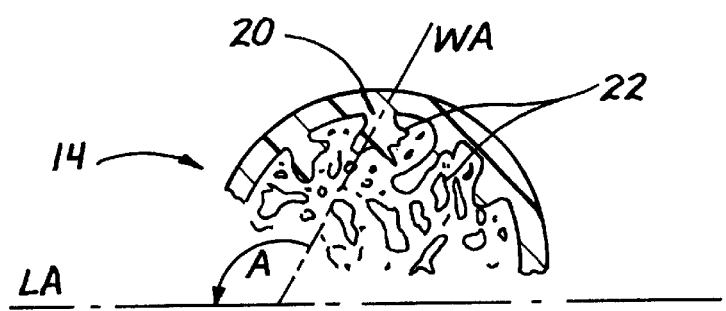
FIG. 4 is an enlarged view of portion 4 of FIG. 3.

As shown in FIGS. 2 and 4, it will be further appreciated that, in at least some embodiments of the invention (e.g., guidewires, scopes, catheters, other elongate devices that are insertable and retractable into and out of the body), the medical device will have a longitudinal axis LA along which the device is typically advanced and retracted. A wall axis WA projected parallel to a portion of a wall of a cavity 20 (e.g., slot, pore, groove, aperture or other opening or depression) within which the polymer is deposited may be perpendicular, nearly perpendicular or non-parallel to the longitudinal axis, as shown. Preferably, the angle A between the longitudinal axis LA and wall axis WA will be at least 75 degrees and preferably at least 90 degrees. In cases where the angle A is greater than 90 degrees, an undercut will be created and such undercut will create a firm mechanical interlock between the coating 20 and the surface of the working element (e.g., the body 12 of the guidewire, catheter, scope, probe, wire, electrode, sensor, etc.). In these embodiments, any slippage or separation of the polymer coating 20 from the device 10 would require the polymer coating 20 to move outwardly along the wall axis WA in order for the coating 20 to pull out of the cavities 22 into which it is deposited. Since this wall axis WA is non-parallel to the longitudinal axis of the device, routine advancement and retraction of the device along its longitudinal axis will not facilitate unwanted slippage or movement of the polymer in the direction of the wall axis and the penetration or extension of the coating 20 into the cavities 22 will reduce the potential for unwanted longitudinal slippage or separation of the polymer coating 20 from the device 10 as the device 10 is routinely advanced into and retracted from the patient's body.

Variations of the working element and/or variations in the types of cavities formed in its surface are shown in FIGS. 5–8. Specifically, FIG. 5 shows a section of another guidewire 30 which comprises a helically would coil of relatively non-porous steel wire 32 having a polymer coating 34 disposed on the outer surface 38 thereof. An optional tubular core member 36 is positioned within the coiled wire 32. The outer surface 38 of the wire 32 has been treated by a mechanical abrasion process or chemical etching by an acid or other chemical which results in microtexturing of the outer surface, as shown. This microtextured outer surface 38 has cavities 39 (e.g., indentations, pits, depressions, grooves, a single helical or curved groove, etc.) formed therein. The coating 34 has entered some or all of the cavities 39, thereby creating a mechanical interlock between the outer surface 38 of the device 30 and the coating 34.

FIG. 6 shows a substantially solid member 42, such as a probe or scope, which has generally rectangular cavities in the nature of slots 46 formed inwardly from the outer surface 47 thereof. A polymer coating 44 is disposed continuously over the outer surface 47 of the solid member 42. A longitudinal axis LA is projectable through the solid member 42. A wall axis WA is projectable along the side wall 48 of each slot 46. For at least some of the slots 46, the wall axis WA is substantially perpendicular to the longitudinal axis LA, such that angle A will be approximately 90 degrees, as shown in FIG. 6. It will be appreciated that, in some embodiments, the side walls 48 of at least some slots 46 may be slanted or angled such that the slot 46 is wider at its bottom B than at its top T, thereby creating an undercut which further mechanically locks or frictionally engages the coating 44 to the solid member 42.

FIG. 7 shows yet another example of the present invention. In the example of FIG. 7, the working element of the device comprises a tubular catheter or cannula 50. A metal tube 53 which has slots or holes 58 formed therein is used as a backbone for the catheter or cannula 50. A mandrel or other space occupying member (not shown) is placed within the area of the lumen 56 and a polymer coating 54 is applied such that the polymer coating 54 permeates though the slots 58 and into contact with the mandrel or other space occupying member. After the coating has solidified, the mandrel or other space occupying member is removed to create the lumen 56. The polymer coating 54 thus creates a continuous sidewall of the tubular catheter or cannula 50 with the slotted metal tube 52 forming a backbone, skeleton or scaffold for the polymer coating.

FIG. 8 shows yet another example of the present invention. In the example of FIG. 8, the working element of the device 60 comprises a tubular catheter body 62 formed of a plastic material and having a lumen 66 extending longitudinally therethrough. Cavities 68, in the nature of blind bore holes, slots or groves, extend downwardly from the outer surface 69 of the catheter body 62 but do not penetrate into the lumen 66. Quantities of coating 64 are deposited in each cavity 62 and protrude upwardly above the outer surface of the catheter 69. The quantities of coating 64 may be discreet and unconnected to one another, as shown in FIG. 8, to thereby form a non-continuous coating comprising a system of rased knobs, bumps, ridges, etc. The coating 64 may be deposited into the cavities 68 so that a meniscus or heap of coating 64 protrudes out of the top of each cavity 68. Alternatively, the coating 64 may be a swellable or expandable coating such as a hydrophilic material (e.g., a hydrogel) and such coating 64 may be initially deposited within each cavity 62 such that the top surface of the coating 64 is flush with or below the adjacent outer surface 69 of the catheter body 62 and such coating 64 may subsequently swell of expand such that it will protrude upwardly above the adjacent outer surface 69, as desired. Such selling or expansion may, in some embodiments, occur when the coating 64 is in contact with a liquid or body fluid for sufficient time to cause the desired swelling or expansion of the coating 64.

Figure 9A:
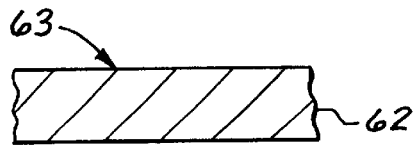
FIGS. 9a–9d show, in step by step fashion, a method for manufacturing a device having a polymer coating disposed thereon in the manner shown in FIG. 8.
Figure 9B:
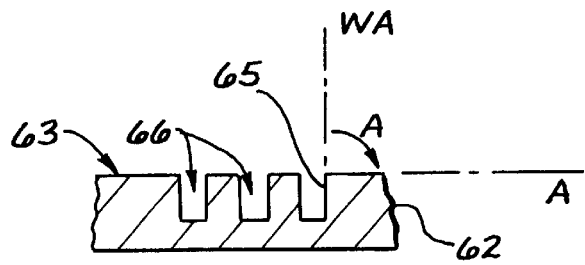
Figure 9C:
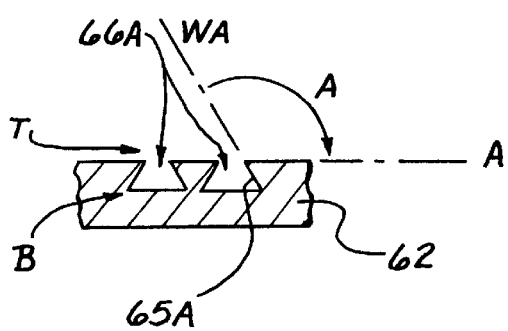
Figure 9C:
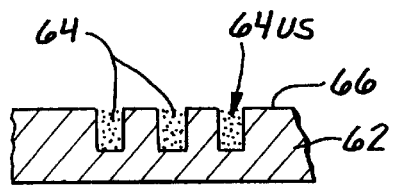
Figure 9D:
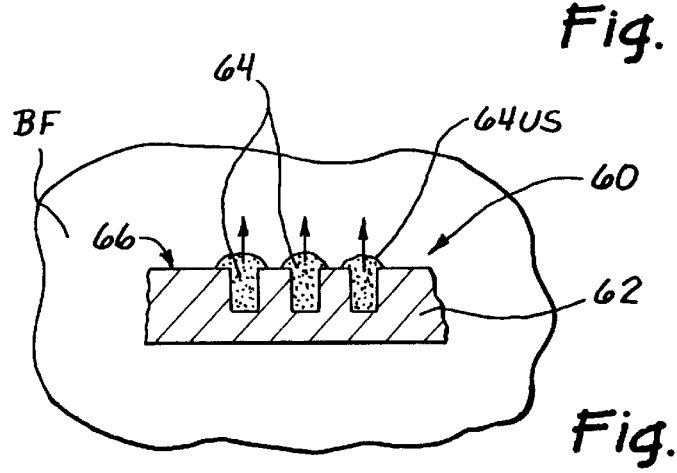

FIGS. 9a–9d show, in step by step fashion, a method for manufacturing a device having non-continuous, discrete deposits of a polymer coating, such as the device 60 of FIG. 8. In this method, a working element such as a wire, a guidewire, a tube, a catheter, a cannula, a scope (e.g., rigid or flexible endoscope, laparoscope, sigmoidoscope, cystoscope, etc.) a probe, an apparatus for collecting information from a location within the body (e.g., an electrode, sensor, camera, scope, sample withdrawal apparatus, biopsy or tissue sampling device, etc.) formed of any suitable material such as metal or plastic is initially provided as shown in FIG. 9a. A plurality of cavities 66 such as blind bore holes, slots, indentations, depressions, cuts, grooves, etc. are formed in the outer surface 62 of the working element 62. This may be accomplished by any technique known in the art such as mechanical drilling, boring, laser etching, cutting, EDM, photochemical etching, etc. As shown in FIG. 9b, wall axes WA projected parallel to at least portions of the sidewalls 65 of at least some of the cavities 66 preferably form an angle A relative to the longitudinal axis LA of the working element or a longitudinal axis of the working element's outer surface 63 are preferably greater than 75 degrees and more preferably greater than 90 degrees. In some embodiments, as shown in FIG. 9b (alt) the sidewalls 65a of the cavities 66a may be angled or curved such that the cavities 66a are wider at their bases B than at their tops T. This results in the formation of an angle A greater than 90 degrees and forms an undercut whereby the later-applied coating 64 (FIGS. 9c–9d) becomes mechanically or frictionally interlocked or engaged by the sidewalls 65a of the cavities 66a.

After the cavities 66 or 66a have been formed in the working element 65, polymer coating 64 is deposited in the cavities 66 or 66a. In some embodiments, such as the specific example shown in FIGS. 9c–9d, the coating 64 is a swellable or expandable coating 64 which swells or expands after coming in contact with a body fluid BF such as blood or other liquid such as saline solution or sterile water. The coating 64 may be initially applied over the entire outer surface 66 of the working element 62 and the layer of coating deposited on the outer surface may then be wiped or scraped away, or otherwise removed, leaving discrete deposits of coating 64 within the cavities 66 such that the upper surface 64 us of each mass of coating 64 is substantially flush with or even slightly below the level of the outer surface 66.

Thereafter, when the working element 62 is immersed in blood or other body fluid BF or when it is immersed in of contacted by a liquid (saline, water, etc.), the deposits of polymer coating 64 will expand or swells such that the upper surface US of each coating deposit 64 protrudes above the outer surface 66 of the working element 62. Alternatively, the polymer coating may expand in response to changes in its environment, such as changes in pH. In this manner, the expansion of the polymer coating creates a non-continuous coating system which comprises discrete raised knobs, bumps, ridges, etc. of polymer coating 64, on the outer surface 66 of the working element 62. Such coating 64 may impart lubricity or form a slippery substance which facilitates the desired insertion, positioning, movement and/or withdrawal of the working element 62 from the body of a human or veterinary patient.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. For example, the particular elements and attributes of any particular embodiment or example may be combined with or substituted for elements or attributes of any other embodiment wherever such addition or substitution does not render the resultant device unuseable or unsuitable for its intended application. Also, although specific types of coating have been referred to herein, many other types of lubricious, non-lubricious, hydrophilic and/or hydrophobic coatings may be used in devices of this invention. Accordingly, it is intended that all such additions, deletions, modifications and other changes be included within the scope of the following claims.

What is claimed is:

1. A medical device that is insertable into the body of a human or veterinary patient, said device comprising:
    a working element having an outer surface;
    a lubricious polymer coating disposed on at least a portion of the outer surface of the working element;
    the outer surface of said working element having cavities formed therein, at least some of said cavities having side walls which are disposed at angles of about 75 or more degrees relative to the outer surface of the working element immediately adjacent to side walls; and,
    at least a portion of said lubricious polymer coating extending into said cavities so as to deter separation of the polymer coating from the working element.

2. A device according to claim 1 wherein the working element comprises a catheter or cannula.

3. A device according to claim 1 wherein the working element comprises a guidewire.

4. A device according to claim 1 wherein the working element comprises a scope.

5. A device according to claim 1 wherein the working element comprises an apparatus for obtaining information from a location within the patient's body.

6. A device according to claim 1 wherein the polymer coating becomes lubricious upon contact with a liquid.

7. A device according to claim 1 wherein the polymer coating comprises a hydrogel.

8. A device according to claim 1 wherein the polymer coating comprises a porous hydrogel.

9. A device according to claim 1 wherein the polymer coating expands in the presence of liquid.

10. A device according to claim 1 wherein the cavities formed in the outer surface of the working element comprise pores.

11. A device according to claim 1 wherein the cavities formed in the outer surface of the working element comprise grooves.

12. A device according to claim 1 wherein the cavities formed in the outer surface of the working element comprise depressions.

13. A device according to claim 1 wherein the cavities formed in the outer surface of the working element comprise indentations.

14. A device according to claim 1 wherein the cavities formed in the outer surface of the working element comprise holes.

15. A device according to claim 1 wherein the cavities formed in the outer surface of the working element comprise slots.

16. A device according to claim 1 wherein the cavities formed in the outer surface of the working element extend only partially into the working element.

17. A device according to claim 1 wherein the cavities formed in the outer surface of the working element extend through the working element.

18. A device according to claim 1 wherein the porosity of the polymer coating is at least about 50%.

19. A device according to claim 1 wherein the polymer coating extends into cavities at least 0.001 inch below the outer surface.

20. A device according to claim 1 wherein the polymer coating extends into cavities such that the polymer coating extends to a depth below the outer surface that is at least about 25% of the total thickness of the polymer coating at that location.

21. A device according to claim 20 wherein the porosity of the polymer coating, when substantially fully expanded, is between about 50% and about 95%.

22. A device according to claim 1 where in substantially all of the polymer coating is initially contained within the cavities and such polymer coating subsequently expands such that a portion of said polymer coating protrudes out of the cavities.

23. A device according to claim 1 wherein substantially all of the polymer coating is initially contained within the cavities beneath the outer surface and such polymer coating subsequently expands such that a portion of said polymer coating protrudes out of the cavities and above the outer surface.

24. A device according to claim 1 wherein the polymer coating comprises a fluorocarbon.

25. A device according to claim 1 wherein the polymer coating comprises polytetrafluoroethylene.

26. A device according to claim 1 wherein the angle is at least 90 degrees.

27. A device according to claim 1 wherein the angle is greater than 90 degrees thereby creating an undercut surface.

28. A device according to claim 1 wherein the polymer coating expands when in contact with a liquid.

29. A device according to claim 1 wherein the polymer coating comprises a hydrogel that expands when in contact with a liquid.

30. A medical device that is insertable into the body of a human or veterinary patient, said device comprising:
   a working element having an outer surface;
   a polymer coating that expands when in contact with a liquid, said polymer coating being disposed on at least a portion of the outer surface of the working element;
   the outer surface of said working element having cavities formed therein, at least some of said cavities having side walls which are disposed at angles of about 75 or more degrees relative to the outer surface of the working element immediately adjacent to side walls; and,
   at least a portion of said polymer coating extending into said cavities so as to deter separation of the polymer coating from the working element.

31. A device according to claim 30 wherein the working element comprises a catheter or cannula.

32. A device according to claim 30 wherein the working element comprises a guidewire.

33. A device according to claim 30 wherein the working element comprises a scope.

34. A device according to claim 30 wherein the working element comprises an apparatus for obtaining information from a location within the patient's body.

35. A device according to claim 30 wherein the polymer coating is lubricious.

36. A device according to claim 30 wherein the polymer coating becomes lubricious upon contact with a liquid.

37. A device according to claim 30 wherein the polymer coating comprises a hydrogel.

38. A device according to claim 30 wherein the polymer coating comprises a porous hydrogel.

39. A device according to claim 30 wherein the cavities formed in the outer surface of the working element comprise pores.

40. A device according to claim 30 wherein the cavities formed in the outer surface of the working element comprise grooves.

41. A device according to claim 30 wherein the cavities formed in the outer surface of the working element comprise depressions.

42. A device according to claim 30 wherein the cavities formed in the outer surface of the working element comprise indentations.

43. A device according to claim 30 wherein the cavities formed in the outer surface of the working element comprise holes.

44. A device according to claim 30 wherein the cavities formed in the outer surface of the working element comprise slots.

45. A device according to claim 30 wherein the cavities formed in the outer surface of the working element extend only partially into the working element.

46. A device according to claim 30 wherein the cavities formed in the outer surface of the working element extend through the working element.

47. A device according to claim 30 wherein the porosity of the polymer coating is at least about 50%.

48. A device according to claim 30 wherein the polymer coating extends into cavities at least 0.001 inch below the outer surface.

49. A device according to claim 30 wherein the polymer coating extends into cavities such that the polymer coating extends to a depth below the outer surface that is at least about 25% of the total thickness of the polymer coating at that location.

50. A device according to claim 30 wherein the porosity of the polymer coating, when substantially fully expanded, is between about 50% and about 95%.

51. A device according to claim 30 wherein substantially all of the polymer coating is initially contained within the cavities and such polymer coating subsequently expands such that a portion of said polymer coating protrudes out of the cavities.

52. A device according to claim 30 wherein substantially all of the polymer coating is initially contained within the cavities beneath the outer surface and such polymer coating subsequently expands such that a portion of said polymer coating protrudes out of the cavities and above the outer surface.

53. A device according to claim 30 wherein the polymer coating comprises a fluorocarbon.

54. A device according to claim 30 wherein the polymer coating comprises polytetrafluoroethylene.

55. A device according to claim 30 wherein the angle is at least 90 degrees.

56. A device according to claim 30 wherein the angle is greater than 90 degrees thereby creating an undercut surface.

57. A device according to claim 30 wherein the polymer coating comprises a hydrogel.

* * * * *